(12) United States Patent
Spanke et al.

(10) Patent No.: US 7,255,006 B2
(45) Date of Patent: Aug. 14, 2007

(54) MEASURING INSTRUMENT

(75) Inventors: Dietmar Spanke, Steinen (DE); Holger Steltner, Freiburg (DE); Fabrice Peter, Blotzheim (FR); Bernhard Ottenbreit, Schörstadt (DE)

(73) Assignee: Endress +Hauser GmbH + Co. KG, Maulburg (DE)

( * ) Notice: Subject to any disclaimer, the term of this patent is extended or adjusted under 35 U.S.C. 154(b) by 0 days.

(21) Appl. No.: 10/849,128

(22) Filed: May 20, 2004

(65) Prior Publication Data

US 2005/0039533 A1 Feb. 24, 2005

(30) Foreign Application Priority Data

May 20, 2003 (DE) ................ 103 23 062

(51) Int. Cl.
*G01N 29/04* (2006.01)
(52) U.S. Cl. .................. 73/587; 593/611; 593/660
(58) Field of Classification Search ........... 73/611, 73/587, 593, 612, 614, 290 R, 579, 599, 73/602, 660, 652, 658, 116, 117.2, 117.3, 73/659

See application file for complete search history.

(56) References Cited

U.S. PATENT DOCUMENTS

| | | | |
|---|---|---|---|
| 4,271,371 A | * 6/1981 | Furuichi et al. ....... 310/316.01 |
| 4,467,271 A | 8/1984 | Ruckenbauer et al. ........ 324/56 |
| 5,156,050 A | * 10/1992 | Schmid et al. ................ 73/628 |
| 5,329,821 A | * 7/1994 | Birnbaum et al. ....... 73/861.28 |
| 5,625,343 A | 4/1997 | Rottmar ..................... 340/620 |
| 5,824,892 A | * 10/1998 | Ishii ............................ 73/149 |
| 6,138,507 A | * 10/2000 | Getman et al. ........... 73/290 V |
| 6,141,625 A | * 10/2000 | Smith et al. ................. 702/50 |
| 6,148,665 A | * 11/2000 | Getman et al. ........... 73/290 V |
| 6,536,553 B1 * | 3/2003 | Scanlon ...................... 181/108 |
| 6,668,650 B1 * | 12/2003 | Lafleur et al. ............... 73/571 |
| 6,840,233 B2 * | 1/2005 | Lingenhult et al. ........ 123/519 |
| 2003/0038644 A1 | 2/2003 | Kleven |
| 2004/0050163 A1 * | 3/2004 | Komninos |

FOREIGN PATENT DOCUMENTS

DE 4232719 A1 5/1994
EP 000981202 A2 * 7/1999

* cited by examiner

*Primary Examiner*—Hezron Williams
*Assistant Examiner*—Jacques M Saint-Surin
(74) *Attorney, Agent, or Firm*—Bacon & Thomas, PLLC

(57) ABSTRACT

A measuring instrument is provided, to which various ultrasonic sensors can be connected in a simple way. The measuring instrument has an electronic measuring instrument unit, to which various ultrasonic sensors can be connected, and having an apparatus for detecting the ultrasonic sensor that is connected, which apparatus, for detecting the ultrasonic sensor, causes the ultrasonic sensor to oscillate, picks up its oscillation behavior, and from that derives a sensor-specific variable.

8 Claims, 3 Drawing Sheets

MEASURING INSTRUMENT

FIELD OF THE INVENTION

The invention relates to a measuring instrument having an electronic measuring instrument unit, to which ultrasonic sensors with different resonant frequencies can be connected.

BACKGROUND OF THE INVENTION

Measuring instruments with ultrasonic sensors are used in many applications. For instance, ultrasonic sensors are used as transmitters and/or receivers in fill level measuring instruments for distance measurement on the principle of echo sounding.

With fill level measuring instruments, among other things fill levels of a product in a container, for instance, or in an open channel can be measured. A signal emitted by the ultrasonic sensor, for instance a brief ultrasonic wave pulse, is transmitted in the direction of the product and is reflected from the surface of the product. The transit time of the pulse from the sensor to the surface and back is ascertained, and from that the fill level or fill height is determined.

Such measuring instruments are used in many branches of industry, such as in the food industry, in the fields of water supply and wastewater treatment, and in chemistry.

Depending on the transmission power and range desired, ultrasonic sensor with different resonant frequencies are employed. Typically, the resonant frequencies are in a range from 1 kHz to 200 kHz.

Measuring instruments therefore advantageously have an electronic measuring instrument unit, to which various ultrasonic sensors can be connected.

Before the measuring instrument can be put into operation, it must be ascertained which ultrasonic sensor is connected to it. This is preferably done automatically, by equipping the measuring instrument with an apparatus for detecting which ultrasonic sensor is connected, and this apparatus performs that task.

In conventional measuring instruments, ultrasonic sensors are therefore equipped with an identification resistor. When the ultrasonic sensor is connected, the identification resistor is simultaneously connected to a resistance measuring circuit, which from the resistance of the identification resistor determines which ultrasonic sensor is connected.

However, this method is quite complicated. The resistor must first be furnished, and two connection lines must be provided for the identification resistor and connected.

Another factor is that ultrasonic sensors without an identification resistor cannot be detected.

SUMMARY OF THE INVENTION

It is an object of the invention to disclose a measuring instrument to which different ultrasonic sensors can be connected in a simple way.

To that end, the invention comprises a measuring instrument, having
an electronic measuring instrument unit,
to which various ultrasonic sensors can be connected, and
an apparatus for detecting the ultrasonic sensor that is connected,
which for detecting the ultrasonic sensor causes the ultrasonic sensor to oscillate, picks up its oscillation behavior, and from that derives a sensor-specific variable.

In this embodiment, there is a connection between the ultrasonic sensor and the electronic measuring instrument unit, by way of which connection
the apparatus for detecting the ultrasonic sensor that is connected can cause the ultrasonic sensor (5) to oscillate and can pick up its oscillation behavior, and
the ultrasonic sensor is connected, in the measurement mode.

The invention further comprises a method for detecting a ultrasonic sensor that is connected to a measuring instrument of the invention, in which
the ultrasonic sensor is excited to oscillation at a predetermined frequency and a predetermined amplitude,
after a fixed time after the termination of the excitation, the amplitude of the oscillation of the ultrasonic sensor is picked up and
from the amplitude, the ultrasonic sensor is determined, by comparing the amplitude with sensor-specific amplitudes stored in memory in a table.

The invention further comprises a method for detecting a ultrasonic sensor that is connected to a measuring instrument of the invention, in which
the ultrasonic sensor is excited to oscillation,
after the termination of the excitation, a development of the amplitude of the oscillation of the ultrasonic sensor is picked up,
from the development, a decay time at which the amplitude decreases exponentially is determined, and
by means of the decay time, the ultrasonic sensor is determined, by comparing the decay time with sensor-specific decay times stored in memory in a table.

The invention further comprises a method for detecting a ultrasonic sensor that is connected to a measuring instrument of the invention, in which
the ultrasonic sensor is excited to oscillation, and
after the termination of the excitation, a frequency or a period length of the oscillation of the ultrasonic sensor is picked up.

The invention further comprises a method for detecting a ultrasonic sensor that is connected to a measuring instrument of the invention, in which
the ultrasonic sensor is excited to oscillation at a predetermined frequency and a predetermined amplitude,
after the termination of the excitation, the signals of the ultrasonic sensor are picked up for a predetermined period of time, and
from that a measure for an oscillation energy of the ultrasonic sensor during this period of time is derived, from which the ultrasonic sensor is detected.

In an embodiment of this last-mentioned method, the signals are rectified, and an integral over the rectified signals or an envelope curve the rectified signals is calculated.

In an embodiment of the measuring instrument,
the apparatus includes a device by which the ultrasonic sensor that is connected can be excited to oscillation and
for each ultrasonic sensor that it can detect, has one associated test branch, to which signals received from whichever ultrasonic sensor is connected can be applied, and each test branch has a bandpass filter, which is passable to a resonant frequency of the associated ultrasonic sensor, and each test branch has a pickup unit that picks up signals that pass through the filter.

The invention and further advantages will now be described in further detail in conjunction with the drawings, in which two exemplary embodiments are shown; the same elements are identified by the same reference numerals throughout the drawings.

DESCRIPTION OF THE PREFERRED EMBODIMENT

Figure 1:
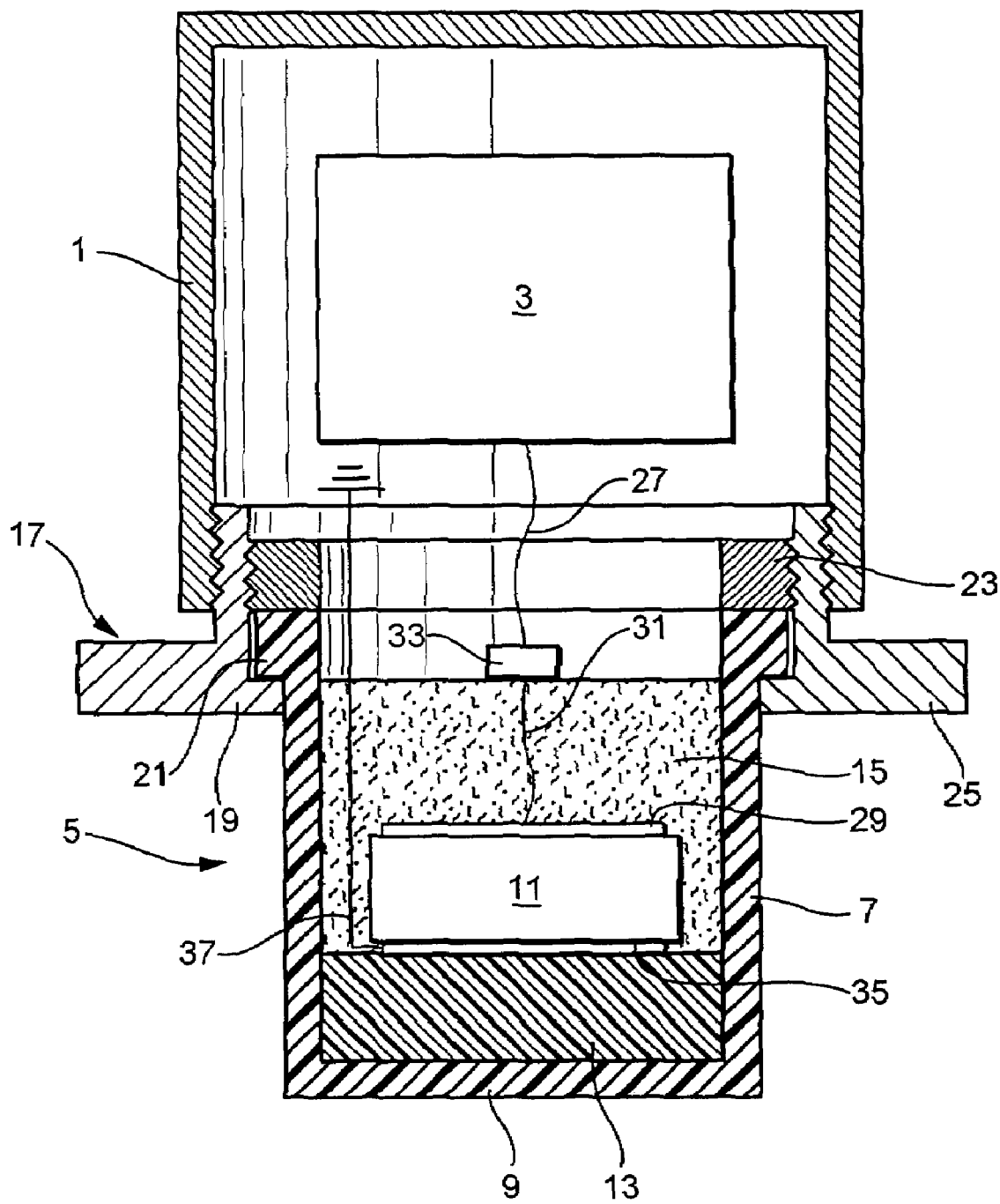
FIG. 1 is a longitudinal section through a measuring instrument with an ultrasonic sensor.

FIG. 1 is a longitudinal section through a measuring instrument of the invention. It includes a measuring instrument housing 1, in which an electronic measuring instrument unit 3 is disposed. The measuring instrument housing is of metal, such as a special steel.

An ultrasonic sensor 5 is connected to the measuring instrument housing 1.

The ultrasonic sensor 5 has a cup-shaped housing 7, which is closed off by a bottom 9.

The housing is of a plastic, such as polypropylene. A piezoelectric element 11 is disposed in the housing 7 and serves to generate and/or pick up ultrasound through the bottom 9.

Since the acoustical impedance of the medium into which the ultrasound is to be transmitted, such as air, and that of the piezoelectric element 11 differ quite sharply from one another, an adaptation layer 13 comprising a plastic with medium acoustical impedance is disposed upstream of the piezoelectric element 11. As the plastic, an epoxy resin is suitable, for instance. In the exemplary embodiment shown, the piezoelectric element 11 is disk-shaped. The adaptation layer 13 is likewise disk-shaped and is located between the piezoelectric element 11 and the bottom 9 of the housing 7.

To attain the best possible adaptation and thus the highest possible acoustic pressure, the adaptation layer 13 preferably has a thickness that is equivalent to one-fourth the wavelength of the sound or ultrasound waves generated.

In an ultrasonic sensor 5 that is used not only as a transmitter but also as a receiver, it is important that any transmission oscillation, once excited, decay rapidly. Not until the transmission oscillation has decayed completely is the ultrasonic sensor ready to receive. To attain fast decay of the transmission oscillation, a damping material 15 is therefore preferably provided in the housing 7. The damping material 15 is for instance a potting material, such as a silicone gel, that completely fills the housing 7.

The measuring instrument is of modular construction. To that end, the ultrasonic sensor 5 is fitted into a mount 17. The mount 17 has a cylindrical portion with a radially inward-extending shoulder 19 integrally formed onto its end. The housing 7, on its end remote from the bottom 9, has a radially outward-extending heel 21, which rests on the shoulder 19. A female thread is provided in the interior of the mount 17 and a pressure ring 23 is screwed into to. The pressure ring 23 rests on the heel 21 and thus fixes the housing 7 in the mount 17. The measuring instrument housing 1 is screwed on the outside onto the cylindrical portion of the mount 17. In addition, a radially outward-extending flange 25 is integrally formed onto the mount 17, and with this flange the measuring instrument can be installed at a site where it is to be used. It is understood that still other modular designs are also possible.

The electronic measuring instrument unit 3 is connected to the ultrasonic sensor 5 via a connection 27. For that purpose, on the piezoelectric element 11, on its end face toward the electronic measuring instrument unit, there is a disk-like terminal electrode 29, to which a line 31 is connected that leads to a plug connector 33 disposed on the open end of the housing 7. The connection 27 leads from the electronic measuring instrument unit 3 to the plug connector 33.

While in conventional measuring instruments with identification resistors, connecting lines leading to the identification resistor are additionally needed, in the measuring instrument of the invention it is sufficient to have the connection 27 between the electronic measuring instrument unit 3 and the ultrasonic sensor 5. Via this connection 27, both the detection of the connected ultrasonic sensor 5 and the connection of the ultrasonic sensor 5 in the measurement mode are effected.

On an end face, toward the adaptation layer 13, of the piezoelectric element 11, a further electrode 35 is provided, to which a connecting line 37 is connected. Via the connecting line 37, the electrode 35 is connected to ground or to a fixed reference potential.

The electronic measuring instrument unit 3 serves to trigger the ultrasonic sensor 5. The electronic measuring instrument unit 3 can be used for both transmitting and receiving ultrasonic signals.

A connected ultrasonic sensor 5 can be exchanged, simply by being mechanically disconnected from the measuring instrument housing 1 and replaced with another ultrasonic sensor 5.

Depending on the application involved, various ultrasonic sensors 5 can be connected to the electronic measuring instrument unit 3. The connectable ultrasonic sensors 5 differ in sensor-specific variables, such as their resonant frequency.

So that the electronic measuring instrument unit 3 will detect which ultrasonic sensor 5 is connected, an apparatus for detecting the ultrasonic sensor 5 that is connected is provided, which to detect the ultrasonic sensor 5 puts the ultrasonic sensor 5 into oscillation, picks up its oscillation behavior, and from that derives a sensor-specific variable.

This is done via the connection 27 between the ultrasonic sensor 3 and the electronic measuring instrument unit 3, by way of which connection the apparatus puts the ultrasonic sensor 5 into oscillation and can pick up its oscillation behavior.

Figure 2:
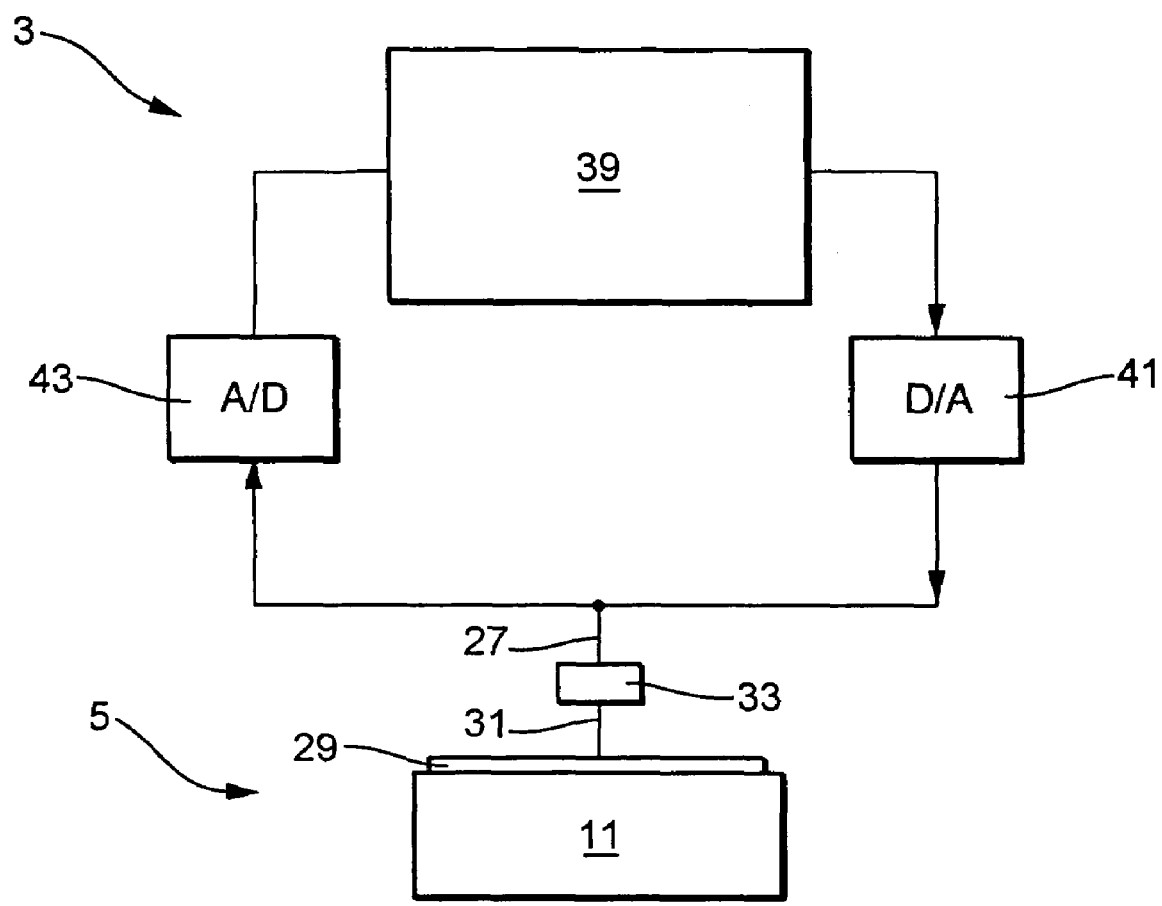
FIG. 2 is a circuit diagram of an electronic measuring instrument unit with a digital signal processor.

FIG. 2 shows an exemplary embodiment for a circuit diagram of an electronic measuring instrument unit 3 connected to the ultrasonic sensor 5 via the connection 27. It includes a digital signal processor 39. The digital signal processor 39 is connected to the ultrasonic sensor 5 via a digital/analog converter 41 and the connecting line 27. The digital signal processor 39 can generate digital signals, which are converted into analog signals via the digital/analog converter 41 and are applied in analog form to the ultrasonic sensor 5. The analog signals put the piezoelectric element 11 into oscillation.

The oscillation behavior of the ultrasonic sensor 5, in the circuit shown, is delivered via the connection 27 to an analog/digital converter 43 connected to it, which digitizes the incoming signals and sends them to the digital signal processor 39.

If ultrasonic signals are transmitted and/or received in the range from 1 kHz to 200 kHz, as is usual in modern ultrasonic measurement technology, then commercially available analog/digital converters and digital/analog converters with sampling rates of about 1 MHz can be used. At present, digital signal processors with clock speeds of several Gigahertz are commercially available; they are fast enough that they are able not only to furnish the signals for exciting the ultrasonic sensor 5, but also to record the oscillation behavior of the ultrasonic sensor 5 directly and process it.

If the measuring instrument is used as a fill level measuring instrument, then for instance as described above a brief ultrasonic wave pulse is generated and sent by the ultrasonic sensor 5 toward the product filling the container or the like. After a transit time that is dependent on the fill level, its echo signal is received and is evaluated by means of the digital signal processor 39.

In the exemplary embodiment shown, the apparatus for detecting the ultrasonic sensor that is connected is preferably integrated with the digital signal processor 39. For that purpose, a program may for instance be provided that is run when the measuring instrument is switched on, before the first measurement is made.

The program serves to perform a method for detecting the ultrasonic sensor 5 that is connected to the measuring instrument. Various methods are possible that put the ultrasonic sensor into oscillation, pick up its oscillation behavior, and from that derive a sensor-specific variable.

Ultrasonic sensors are damped systems capable of oscillation, whose oscillation properties are determined essentially by their quality Q and a natural frequency $f_0$ of the corresponding system without damping.

If the ultrasonic sensor 5, or more precisely the piezoelectric element 11, is set to oscillation with a signal S of the following form, $$S = A_s \cos(2\pi f\, t),$$

in which $A_s$ stands for the amplitude of the excitation,
f stands for the frequency of the excitation, and
t stands for time, then the ultrasonic sensor, after a transient response, executes a forced oscillation of the following form:

$$x(t) = a(A_s, f, f_0, Q) \cos(2\pi f\, t - \alpha(f, f_0, Q)),$$

in which $A(A_s, f, f_0, Q)$ stands for the amplitude of the forced oscillation, which amplitude is dependent on the amplitude $A_s$ of the excitation, the frequency f of the excitation, the natural frequency $f_0$, and the quality Q of the system, and $\alpha(f, f_0, Q)$ stands for the phase, which is dependent on the frequency f of the excitation, the natural frequency $f_0$, and the quality Q of the system.

The amplitude $A(A_s, f, f_0, Q)$ of the forced oscillation is maximal if excitation is done at the resonant frequency $f_{res}$, which is determined from the natural frequency $f_0$ and the quality Q by the following equation:

$$f_{res} = f_0(1 - 1(2Q^2))^{1/2}.$$

If the excitation is stopped at a time $t_0$, then the damped system decays its oscillation oscillate in accordance with the following equation:

$$x_d(t) = e^{-(t-t_0)/T} A(A_s, f, f_0, Q) \cos(2\pi f_d(t-t_0) - \alpha_d,$$

in which $T = Q/\pi f_0$ stands for the decay time,
$f_d = f_0(1 - 1/4Q^2))^{1/2}$ stands for the frequency, and
$\alpha_d$ stands for a phase that is dependent upon starting conditions.

From the oscillation behavior, the ultrasonic sensor 5 that is connected can be detected unambiguously. The identification of the ultrasonic sensor 5 is based on a sensor-specific variable of the ultrasonic sensor 5, such as an amplitude A, established under predetermined conditions, of the oscillation, its decay time T, its frequency $f_0$, or its resonant frequency $f_{res}$.

Four exemplary embodiments of methods for detecting the ultrasonic sensor 5 that is connected, which can be performed by the measuring instrument of the invention described above, will now be described.

In a first method, the ultrasonic sensor is excited to oscillate at a predetermined frequency f and a predetermined amplitude $A_s$. After a fixed time T after the termination of the excitation, the amplitude A(T) of the oscillation of the ultrasonic sensor 5 is picked up. This amplitude A(T) is a sensor-specific variable, on the basis of which the ultrasonic sensor 5 that is connected can be determined. This is preferably done by recording in advance, for all the different ultrasonic sensors 5 provided, the amplitude A(T) at which, once the fixed time T after the termination of the aforementioned excitation at the predetermined frequency f and the predetermined amplitude $A_s$ has elapsed, the ultrasonic sensors oscillate. The amplitude A(T) is stored in memory for each ultrasonic sensor in a table in the measuring instrument.

Upon detection of the ultrasonic sensor 5 that is connection, the sensor-specific value of the amplitude A(T) picked up from that ultrasonic sensor 5 is compared with the values stored in the table. From the comparison, it is directly apparent which ultrasonic sensor 5 is connected.

This method is especially attractive in cases in which the decay times of the connectable ultrasonic sensors 5 are approximately the same.

Once the connected ultrasonic sensor 5 has been ascertained, this ultrasonic sensor is excited, in a form that is optimal for that ultrasonic sensor 5, by the electronic measuring instrument unit 3 in an ensuing measurement mode, In a second method for detecting the ultrasonic sensor 5 that is connected, the ultrasonic sensor 5 is excited to oscillation. This time, the amplitude $A_s$ and frequency f of the excitation need not be fixedly the predetermined.

Once the excitation is terminated, a development of the amplitude of the oscillation of the connected ultrasonic sensor 5 is picked up over a period of time, and a decay time T is determined from this development. As already noted above, the amplitude drops exponentially with the decay time T as the oscillation decays.

This method is especially attractive if the connectable ultrasonic sensors 5 have similar qualities Q.

The decay time T can be determined for instance by measuring the amplitude A(t1) and A(t2) at two different times t1 and t2 after the excitation has been terminated. The decay time T is then determined by the following equation:

$$T = (t2 - t1)/\ln(A(t2)/A(t1)).$$

The decay time T is a sensor-specific variable, from which the connected ultrasonic sensor 5 can be identified perfectly. To that end, a table of the decay times T of the various ultrasonic sensors 5 that can be connected is preferably set up beforehand and stored in a memory in the measuring instrument. The detection of which ultrasonic sensor 5 is connected is then done by comparing the measured decay time T with the sensor-specific decay times T stored in the table.

In a further method for detecting the ultrasonic sensor 5 that is connected, the ultrasonic sensor 5 is excited to oscillate at an arbitrary frequency and an arbitrary amplitude. After the excitation is terminated, a frequency $f_d$ or a period length $T_d$ of the oscillation of the ultrasonic sensor is picked up. The frequency $f_d$ and the period length $T_d$ are inversely proportional to one another and, as noted above, depend on the natural frequency $f_0$ and on the quality Q of the ultrasonic sensor 5. Accordingly, they represent sensor-specific variables, which are suitable for detecting which ultrasonic sensor 5 is connected. The frequency $f_d$ and the period length $T_d$ can for instance be determined by recording an amplitude course of the oscillation once the excitation has been terminated. From zero crossovers and/or the location of minimum and maximum points of the amplitude course, both variables can be ascertained.

The sensor-specific frequencies $f_d$ and/or period lengths $T_d$ have preferably been determined beforehand for all the ultrasonic sensors 5 provided and stored in memory in a table. By a comparison of the measured values with the values stored in the table, the ultrasonic sensor 5 that is connected can be detected.

In a further method for detecting the ultrasonic sensor 5 that is connected, the ultrasonic sensor 5 is excited to oscillate at a predetermined frequency f and a predetermined amplitude $A_s$. Once the excitation is terminated, the signals of the ultrasonic sensor 5 are picked up for a predetermined length of time, and from that a measure for an oscillation energy of the ultrasonic sensor 5 during that length of time is derived. This measure for the oscillation energy forms a sensor-specific variable from which the ultrasonic sensor 5 that is connected can be detected. This exploits the physical effect in which more oscillation energy is transmitted to the ultrasonic sensor and output again by it, the closer the predetermined frequency f at which the excitation is done is to the resonant frequency $f_{res}$ of that ultrasonic sensor.

Preferably, this measure for the oscillation energy is determined by rectifying the signals of the ultrasonic sensor 5 during the predetermined length of time. This yields a signal amplitude as a function of time. An integral over the thus-determined signal amplitude over the predetermined length of time yields a measure for the oscillation energy. Alternatively, an envelope curve can be determined for the rectified signals and the integral can be calculated over the envelope curve.

Analogously to the methods described above, here as well, for all the different ultrasonic sensors 5 that can be used, the measure for the oscillation energy is determined beforehand and stored in memory in the measuring instrument. A simple comparison of the measured value with the values stored in memory beforehand then yields an unambiguous identification of the ultrasonic sensor that is connected. In the exemplary embodiment shown in FIG. 2, all of the signal excitation and signal processing is done in digital form. However, it is also possible to equip measuring instruments of the invention with largely analog signal excitation and signal processing.

Figure 3:
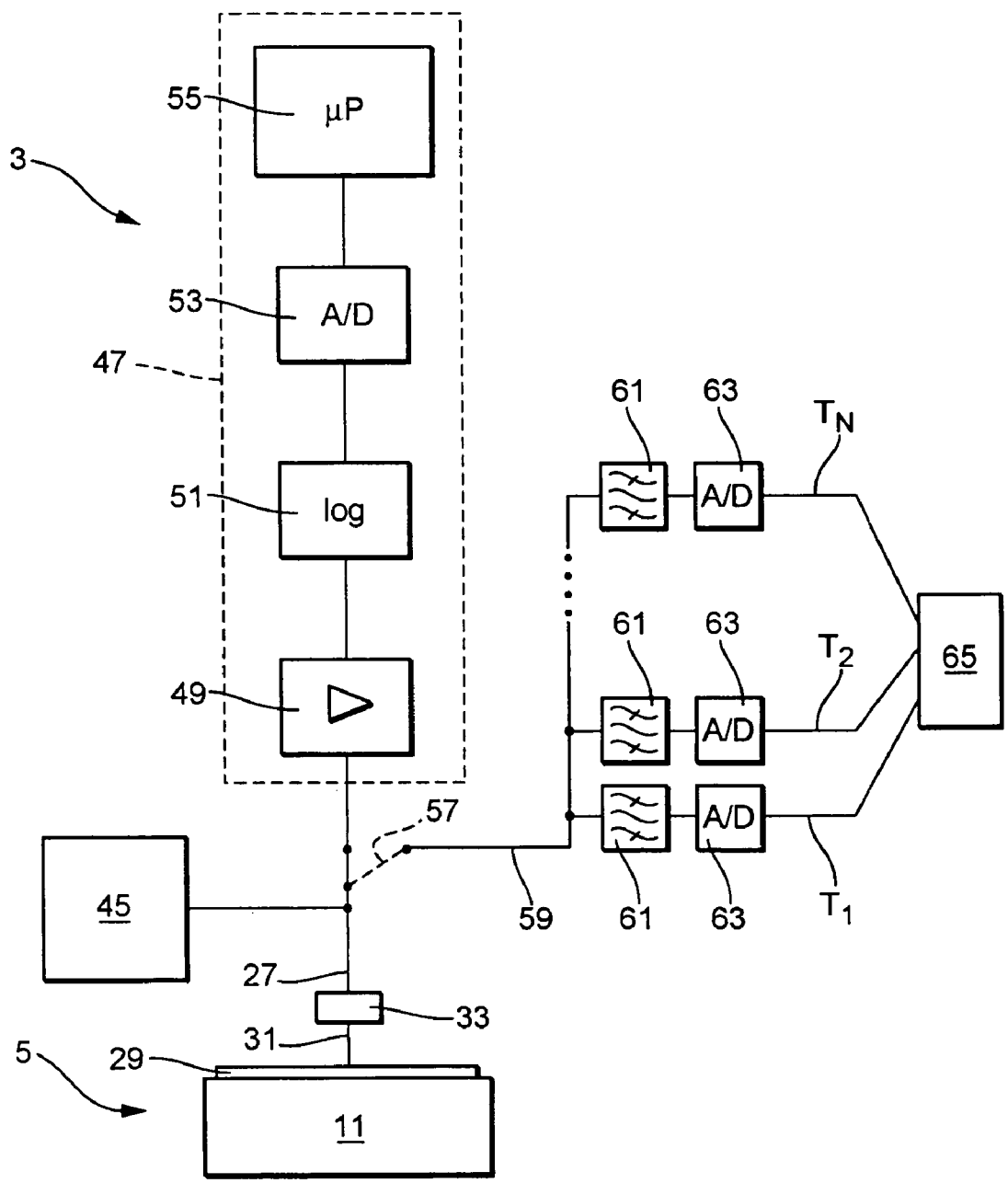
FIG. 3 is a circuit diagram of an electronic measuring instrument unit with a transmission signal generator and a reception circuit.

One exemplary embodiment for a circuit diagram of such a measuring instrument is shown in FIG. 3. FIG. 3 shows a circuit diagram of an electronic measuring instrument unit 3 with a transmission signal generator 45 and a reception circuit 47, of the kind also used in conventional measuring instruments.

The transmission signal generator 45 generates brief pulses, for instance, at the resonant frequency $f_{res}$ of whichever ultrasonic sensor 5 is connected. The signals generated are applied to the ultrasonic sensor 5 via the connecting line 27. Correspondingly, signals received by the ultrasonic sensor 5 are delivered via to the reception circuit 47 the connecting line 27.

The reception circuit 47 has an amplifier 49 and a logarithmation module 51 downstream of it. The signals, straightened by the logarithmation module 51, are made available to an analog/digital converter 53 and by it to a microprocessor 55 for evaluation and/or processing. Because of the analog preprocessing of the incoming signals, an analog/digital converter with a sampling rate of less than 100 kHz suffices.

According to the invention, the measuring instrument includes an apparatus for detecting the ultrasonic sensor that is connected; for detecting the ultrasonic sensor 5, it sets the ultrasonic sensor 5 into oscillation, picks up its oscillation behavior, and from that derives a sensor-specific variable.

This apparatus includes a device by which the ultrasonic sensor 5 that is connected can be excited. Preferably, this device is the transmission signal generator 45, which is connected to the ultrasonic sensor 5 anyway.

The apparatus also, for each ultrasonic sensor 5 that it can detect, has one associated test branch T1 . . . TN, to which signals picked up from whichever ultrasonic sensor 5 is connected can be applied. To that end, a switch 57 is provided, by way of which the signals picked up from the ultrasonic sensor 5 are selectively delivered to either the reception circuit 47 or a supply line 59 leading to the test branches T1 . . . TN.

The various ultrasonic sensors 5 that can be connected differ from one another in their resonant frequencies $f_{res}$. Accordingly, each test branch T1 . . . TN has a bandpass filter 61 that is passable to the resonant frequency $f_{res}$ of the associated ultrasonic sensor 5. Each test branch T1 . . . TN has a pickup unit, which picks up the signals that pass through the bandpass filter 61.

In the exemplary embodiment shown, the pickup unit includes analog/digital converters 63, which are downstream of the bandpass filters 61. The analog/digital converters 63 feed the signals, supplied to them, in digital form into a microprocessor 65, which is also a component of the pickup unit.

In the exemplary embodiment shown, the microprocessors 55 and 65 are two separate components, but it is also possible instead to provide only a single microprocessor, which then replaces the two microprocessors 55 and 65.

If the ultrasonic sensor 5 is excited to oscillation by a signal that has a broad frequency spectrum, then it will pick up the most oscillation energy in the range of its resonant frequency $f_{res}$, and afterward, as its oscillation decays, will also output the most oscillation energy again in that frequency range. Accordingly, the greatest transmission power will be in the test branch T in which the resonant frequency $f_{res}$ of whichever ultrasonic sensor 5 is connected at that time is filtered out. This test branch T is ascertained by means of the microprocessor 65. In the process, the test branch T having the greatest signal amplitude can for instance be determined. It is equally possible for the signal amplitude for each test branch T to be integrated over a predetermined period of time. If the test branch T is known, then the ultrasonic sensor 5 that is connected is also known.

The measuring instrument automatically detects which ultrasonic sensor 5 is connected. Preferably, the detection of the connected ultrasonic sensor 5 is effected automatically every time the measuring instrument is switched on. Once the ultrasonic sensor 5 is detected, it is excited in the measurement mode to transmit, preferably at its resonant frequency $f_{res}$, since at that frequency a high transmission power is attainable, and power losses are slight.

NUMERAL NAME

1 Measuring Instrument Housing
3 Electronic Measuring Instrument Unit
5 Ultrasonic Sensor
7 Housing
9 Bottom
11 Piezoelectric Element
13 Adaptation Layer
15 Damping Layer
17 Mount
19 Shoulder
21 Heel
23 Pressure Ring
25 Flange
27 Connecting Line
29 Terminal Electrode
31 Line
33 Plug Connector
35 Electrode
37 Connecting Line
39 Signal Processor
41 Digital/analog Converter
43 Analog/digital Converter
45 Transmission Signal Generator
47 Reception Circuit
49 Amplifier
51 Logarithmation Module
53 Analog/digital Converter
55 Microprocessor
57 Switch
59 Supply Line
61 Bandpass Filter
63 Analog/digital Converter
65 Microprocessor

The invention claimed is:

1. A measuring instrument, comprising:
an electronic measuring instrument unit,
a replaceable ultrasonic sensor having a sensor-specific variable, said ultrasonic sensor being chosen from a variety of ultrasonic sensors having different sensor-specific variables;
means for connecting said ultrasonic to said electronic measuring instrument unit; and
means for identification of said ultrasonic sensor based on said sensor-specific variable of said ultrasonic sensor connected to said electronic measuring instrument unit, wherein:
said means for identification of said ultrasonic sensor identifies said ultrasonic sensor by causing said ultrasonic sensor to oscillate, picking up the oscillation behavior of said ultrasonic sensor, and from that deriving the sensor-specific variable of said ultrasonic sensor.

2. The measuring instrument of according to claim 1, wherein:
said ultrasonic sensor is connected to said electronic measuring instrument unit via a connection, by way of which connection said means for identification of said ultrasonic sensor identifies said ultrasonic sensor by causing said ultrasonic sensor to oscillate, picking up the oscillation behavior of said ultrasonic sensor, and from that defining the sensor-specific variable of said ultrasonic sensor, in order to identify said connected ultrasonic sensor, and
said ultrasonic sensor is connected to said electronic measuring instrument unit during measurement.

3. The measuring instrument according to claim 1, wherein:
said means for identification includes a device by which said ultrasonic sensor that is connected can be excited to oscillation, said means for identification has, for each ultrasonic sensor that it can identify, one associated test branch, to which signals received from whichever ultrasonic sensor is connected can be applied, each test branch has a bandpass filter, which is passable to a resonant frequency of the associated ultrasonic sensor, and each test branch has a pickup unit that picks up signals that pass through the filter.

4. A method for identifying an ultrasonic sensor of a measuring instrument, wherein: said ultrasonic sensor has a sensor-specific variable, said ultrasonic sensor is chosen from a variety of ultrasonic sensors having different sensor-specific variables, said ultrasonic sensor is connected to a measuring instrument unit of the measuring instrument, and said measuring instrument comprises means for identification of said electronic sensor based on its sensor-specific variable, comprising the steps of:
exciting the ultrasonic sensor to oscillation at a predetermined frequency and a predetermined amplitude;
picking-up the amplitude of the oscillation of the ultrasonic sensor at a fixed time after termination of said excitation;
comparing the amplitude pick-up, with sensor-specific amplitudes stored in memory in a table; and
identifying said connected ultrasonic sensor based on this comparison.

5. The method according to claim 4 for identifying the ultrasonic sensor connected to the measuring instrument unit of the measurement instrument, further comprising the steps of:
picking-up, after termination of said excitation, the signals of the ultrasonic sensor for a predetermined period of time; and
deriving from the signals of the ultrasonic sensor that are picked-up in the predetermined period of time a measure for an oscillation energy of the ultrasonic sensor during this period of time, from which the ultrasonic sensor is identified.

6. The method according to claim 5, wherein:
the signals are rectified; and
an integral over the rectified signals or an envelope curve the rectified signals is calculated.

7. The method for identifying an ultrasonic sensor of a measuring instrument wherein: said ultrasonic sensor has a sensor-specific variable, said ultrasonic sensor is chosen from a variety of ultrasonic sensors having different sensor-specific variables, said ultrasonic sensor is connected to a measuring instrument unit of the measuring instrument, comprising the steps of:

picking-up, after termination of said excitation, a development of the amplitude of the oscillation of the ultrasonic sensor;
determining from said development, a decay time at which the amplitude decreases exponentially;
comparing said decay time with sensor-specific decay times stored in memory in a table; and
identifying said connected ultrasonic sensor based on this comparison.

8. The method according to claim 4 for identifying an ultrasonic sensor that is connected to a measuring instrument unit of a measurement instrument, wherein:

after termination of said excitation, a frequency or a period length of the oscillation of the ultrasonic sensor is picked up.

* * * * *